United States Patent [19]

Leiberich et al.

[11] 3,959,540

[45] May 25, 1976

[54] GASTRIC JUICE RESISTANT GELATIN CAPSULES AND A PROCESS FOR THE PRODUCTION THEREOF

[75] Inventors: Richard Leiberich, Eberbach; Wilfried Gabler, Heidelberg, both of Germany

[73] Assignee: R.P. Scherer GmbH, Eberbach, Baden, Germany

[22] Filed: Aug. 8, 1974

[21] Appl. No.: 495,896

[30] Foreign Application Priority Data

Aug. 8, 1973   Germany............................ 2340060

[52] U.S. Cl..................................... 428/35; 424/33; 427/3; 427/407; 428/407; 428/474; 428/520
[51] Int. Cl.².......................................... A61K 9/58
[58] Field of Search................... 117/141, 72, 94; 424/33; 428/35, 474, 520, 407; 427/3, 407

[56] References Cited
UNITED STATES PATENTS

| | | | |
|---|---|---|---|
| 3,070,509 | 12/1962 | Volker et al........................... | 424/33 |
| 3,592,945 | 7/1971 | Engelking.......................... | 424/33 X |
| 3,656,997 | 4/1972 | Cordes............................. | 117/141 X |

FOREIGN PATENTS OR APPLICATIONS

| | | | |
|---|---|---|---|
| 2,135,073 | 2/1973 | Germany.............................. | 424/33 |

*Primary Examiner*—Ralph Husack
*Attorney, Agent, or Firm*—Armstrong, Nikaido & Wegner

[57] ABSTRACT

Gastric juice resistant gelatin capsules characterized by a gastric juice resistant outer coating of an anionic polymerizate of methacrylic acid and acrylic acid esters and an intermediate layer between the outer layer and the gelatin shell of a cationic polymerizate of di-lower alkylamino lower alkylmethyl acrylate with other neutral methacrylic esters and a process for preparing the same.

7 Claims, No Drawings

GASTRIC JUICE RESISTANT GELATIN CAPSULES AND A PROCESS FOR THE PRODUCTION THEREOF

The present invention relates to gastric juice resistant gelatin capsules which are characterized by a gastric juice resistant outer layer consisting of an anionic polymerizate of methacrylic acid and acrylic acid esters and an intermediate layer consisting of a cationic polymerizate of di-lower alkylamino-lower alkylmethacrylate with other neutral methacrylic acid esters between this outer layer and the gelatin shell and a process for the production thereof.

BACKGROUND OF THE INVENTION

Over the past years gelatin capsules have gained an increasing share of the drug market and this tendency is still increasing. This development has lead to an increase in encapsulated medicaments which must be resistant to gastric juices and are only intended to release their content in the small intestine.

The demands placed on these gastric juice resistant capsules which are soluble in the intestine are becoming increasingly specific: after passing through the stomach, the drug is intended to decompose as rapidly as possible, preferably in the upper part of the duodenum and the active substance is released at the point of maximum reabsorption or of maximum efficiency.

Previously, the gelatin capsules were rendered resistant to gastric juices by treating them with formaldehyde which was caused to react with the gelatin either in gaseous form or in an aqueous solution or in solution with water miscible organic solvents.

It is generally known that the "hardened" gastric juice resistant gelatin capsules produced in this way were unable to withstand strict tests. It is very difficult to adjust the correct level of "hardening." It is also known that the gastric juice resistance and, in particular, the intestinal solubility of the gelatin capsules treated with formaldehyde tended to change in the course of time.

In addition, the intestinal solubility of the gelatin capsules treated with formaldehyde depends on the content of digestive ferments in the intestinal juice and, in particular, on pancreatin, thus causing many difficulties when these were prescribed for people with insufficient digestion.

For these reasons, processes and substances have been developed over the years for applying gastric juice resistant, intestinally soluble coatings to gelatin capsules and to tablets and dragees. The dissolution of these coatings was then exclusively dependent on the pH value of the digestive juices and not on the ferments.

The disadvantage of using the known gastric juice resistant, intestinally soluble, film forming substances such as shellac or celluloseacetate phthalate (CAP) or hydroxypropylmethylcellulose phthalate (HPMCP) or alkyl-half ester of ethylene-maleic acid anhydride co-polymerizates or alkyl half ester of vinylmethylethylmaleic acid anhydride co-polymerizates (see German AS 14 67 875, published Jan. 23, 1969), is that it is necessary to use toxic and/or inflammable solvents or solvent mixtures for producing the lacquer solutions. In addition, shellac and CAP are subject, during storage, to changes in their solubility in intestinal juice in terms of delaying of the dissolution rate of the coated drug blank which in the case of CAP can also be associated with the separating off of acetic acid.

Although the coating of tablets and dragees or dragee cores with gastric juice resistant, intestinally soluble solvent laquers can be effected relatively easily by the known processes owing to their porous surfaces which facilitate adherence of the lacquers, difficulties arise when coating gelatin capsules, for example, with CAP or HPMCP owing to their smooth, non-absorptive surfaces. In particular, these difficulties involve the adhesion of the lacquer and the smoothness, brilliance and transparency of the film of lacquer.

Owing to the need for safe processing and in view of the increasingly stricter environmental protection regulations, efforts were made to obtain gastric juice resistant, intestinally soluble lacquer substances which avoid the need to use toxic and/or inflammable solvents. In the course of research, a gastric juice resistant, intestinally soluble lacquer in the form of an aqueous dispersion of the anionic polymerizate of methacrylic acid and acrylic acid esters, for example, methacrylic acid- acrylic acid ethylester 50:50 copolymerizate = MAC, was found. This is described in German OS 21 35 073, laid open Feb. 1, 1973 and will be referred to hereafter by the abbreviation MAC.

This aqueous dispersion of MAC can easily be applied to medicinal blanks by the known air suspending technique, (for example, Glatt or Glatt-Wurster). However, if this MAC film is applied to gelatin capsules, the gelatin shell becomes so brittle during the subsequent drying process that it decomposes when only slight pressure is applied thereto. Thus the gelatin capsules lose their mechanical stability when they are treated with an aqueous MAC dispersion.

It is not exactly known which mechanism causes this embrittlement. The highly acidic submicroscopic MAC dispersion particles possibly penetrate the gelatin shell and cause the embrittlement therein. It was then found that this embrittlement of the gelatin capsules can be avoided by applying a neutralizing layer between the gelatin shell and the MAC film. This neutralizing layer prevents the penetration into the gelatin shell of the highly acidic submicroscopic dispersion particles.

The term "gelatin capsules" as used in this test is intended to refer both to hard and also soft gelatin capsules.

In German OS 19 24 647, laid open Nov. 19, 1970, it is disclosed that to produce carriagable and storable gastric juice resistant, intestinally soluble capsules, it is possible to spray on a priming lacquer consisting of one or more film forming colloids which are totally or partially soluble both in water and organic solvents and thereafter coating the capsules which have been pretreated in this way with a gastric juice resistant lacquer.

Similarly, a process is disclosed in GB patent 1 190 387, issued May 6, 1970 for producing gastric juice resistant hard gelatin capsules by applying to the gelatin capsules an inner layer of polyvinylpyrrolidone and an outer layer of celluloseacetatephthalate (CAP).

In both cases, it is necessary to use toxic and/or inflammable solvents to dissolve the gastric juice resistant lacquers in question.

The following substances, inter alia, were tested in the course of efforts to find suitable film forming substances which prevent the gelatin shells of the capsules from becoming brittle: reemulsifiable vinylacetate polymers and vinylacetate co-polymers, polyvinylacetate, polyvinylalcohols, polyvinylpyrrolidone, dextrine, modified starches, gum arabic, shellac and cationic polymerizates of di-loweralkyl-amino-lower alkyl-methacrylate with other neutral methacrylic acid esters in aqueous dispersions, in aqueous, aqueous-ammoniacal, aqueous-alcoholic or alcoholic solutions with or without the common physiologically acceptable plasticizers.

SUMMARY OF THE INVENTION

Whereas the intermediate layers of the above-listed film forming substances, with the exception of the latter substance, were either unable to prevent the embrittlement of the gelatin shells of the capsules or were too brittle as film coatings so that the intermediate layers possessed insufficient mechanical stability or did not adhere sufficiently well to the gelatin surface of the capsule or possessed too little adhesion or were incompatible with the gastric juice resistant layer, or did not form a smooth, brilliant, transparent film, it was surprisingly found that by only applying the intermediate layer known as the "neutralization layer" consisting of the cationic polymerizates of di-lower alkyl-amino-lower alkylmethacrylate, wherein lower alkyl preferably refers to an alkyl radical having up to 4 C atoms with other neutral methacrylic acid esters, for example, dimethylaminoethylmethacrylate methacrylic acid butylester-methacrylic acid methylester- 50:30:20 copolymerizate = DMMC - as described in West German patent 1 090 381, published Oct. 6, 1960, the embrittlement of the gelatin shell could be reliably avoided after spraying on the gastric juice resistant layer from the aqueous dispersion of the anionic polymerizate of methacrylic acid and acrylic acid ester.

In addition, it was also found that the intermediate layer known as the "neutralization layer" combines very firmly with the gastric juice resistant layer and that both layers together adhere to the completely smooth non-absorbent gelatin surface of the capsules so firmly that they can no longer be separated mechanically without the gelatin surface being damaged. The lacquer film itself has a high measure of smoothness, brilliance and transparency and it is therefore unnecessary to further process the gastric juice resistant gelatin capsules produced according to the invention.

In addition to the completely reliable gastric juice resistance, an equally surprising feature which could not be predicted was the very easy and rapid intestinal solubility of the gelatin capsules coated according to the invention with the neutralization layer and subsequently with the gastric juice resistant layer as it had been found that gelatin capsules which were only coated with the neutralization layer had totally reversed dissolution properties, namely, complete insolubility in water and artificial intestinal juice USP, but ready solubility in artificial gastric juice USP. After the application of the gastric juice resistant layer consisting of the MAC dispersion, the dissolution properties are totally reversed. The gelatin capsules remain stable for several hours in the highly acidic digestive juices having a pH of up to about 5 and they decompose rapidly in the mildly acid to mildly alkaline digestive juices from a pH of about 6.

The dissolution properties of the latter are reversed by applying the gastric juice resistant layer to the neutralization layer. This indicates that the highly acidic submicroscopic particles of the gastric juice resistant lacquer dispersion are intercepted by the neutralization layer and cannot penetrate the gelatin shell.

The thickness of the neutralization layer must be such that the highly acidic submicroscopic dispersion particles of the gastric juice resistant lacquer dispersion are reliably intercepted before they reach the gelatin shell of the capsules but that no residual film which is insoluble in the intestinal juice remains after the gastric juice resistant layer has been applied; this residual film of the neutralization layer would prevent or delay the decomposition of the gastric juice resistant coated gelatin capsules in the intestinal juice.

To achieve this, the neutralization layer is applied in a quantity of about 0.25 mg – 2.5 mg resin/$cm^2$ of capsule surface.

In addition, the gastric juice resistant coated gelatin capsules are less sensitive to heat and damp than non-coated gelatin capsules.

Common physiologically acceptable substances can be used as plasticizers, both for the isolating layer and for the gastric juice resistant layer. Examples of these physiologically acceptable substances are glycols, for example, ethyleneglycol, 1,2-propyleneglycol, 1,3-butyleneglycol, liquid and solid polyglycols, glycerine, glycerine ester, for example, triacetin, castor oil, glycerolmono-and dioleate, ethoxylated partial glycerides of middle chain fatty acids, phthalic acid ester, adipic acid ester, sebacic acid ester, fatty acid lower alkylesters — individually or in mixtures.

The process for producing the gastric juice resistant gelatin capsules according to the invention consists in first spraying into the capsules a neutralizing or intermediate layer in the form of a very thin pore-free film of cationic polymerizates which are insoluble in water and intestinal juice and soluble in gastric juice; these polymerizates consisting of di-lower alkylamino lower alkylmethacrylate with other neutral methacrylic acid esters, preferably dimethylaminoethylmethacrylatemethacrylic acid butylester-methacrylic acid methylester - 50:30:20- copolymerizate (DMMC) from an aqueous-alcoholic solution and thereafter in applying to the gelatin capsules which have been pretreated in this way the gastric juice resistant film from the aqueous dispersion of anionic polymerizates of methacrylicacid and acrylic ester, preferably methacrylicacid acrylic ethyl ester - 50:50 -copolymerizate (MAC).

In this process, the neutralization layer is applied to the capsules in a quantity of 0.25 mg – 2.5 mg resin/$cm^2$ capsule surface area and the gastric juice resistant layer is applied to the intermediate layer, advantageously in quantities of 2 mg-20mg resin/$cm^2$ capsule surface area.

The layers are preferably applied by the air suspending technique (Glatt or Glatt-Wurster) and both layers can be applied in succession in a single device without interrupting the process.

Dissolution of the intermediate layer is advantageously obtained by adding to the DMMC, 5 – 25% plasticizers relative to the quantity of resin and in dissolving this mixture in lower alcohols having a chain length of $C_1$-$C_3$ and to which water may also be added, in concentrations of 2.5 – 15% relative to the quantity of resin.

The aqueous dispersion for the gastric juice resistant coating consists of 5 – 25% MAC with an added 5–25% plasticizer relative to the amount of MAC.

The following examples will further illustrate the invention:

EXAMPLE 1

Production of the lacquer solution for the intermediate coating 2.5 g DMMC were mixed with 0.125 g castor oil and the resulting mixture dissolved in 97.375 g isopropanol.

EXAMPLE 2

The same process as described in Example 1 was effected using:
5 g DMMC
0.50 g ethoxylated partial glyceride of middle chain fatty acids
56.70 g ethanol and
37.80 g water

EXAMPLE 3

The same process as described in Example 1 was carried out using:
10 g DMMC
1.5 g dibutylphthalate
80 g ethanol and
8.5 g water

EXAMPLE 4

The process according to Example 1 was carried out using:
15 g DMMC
3.75 g glycerine
60.94 g methanol and
20.31 g water.

EXAMPLE 5

The aqueous dispersion for the gastric juice resistant coating was produced from the aqueous dispersion obtained according to West German OS 21 35 075 of MAC with a content of 30% resin by mixing the constituents indicated:
5 g resin of MAC from a 30% dispersion
0.75 g polyglycol 400 and
94.25 g water.

EXAMPLE 6

The process according to Example 5 was carried out using
10 g MAC resin from a 30% dispersion
1 g triacetin and
89 g water.

EXAMPLE 7

The process according to Example 5 was carried out using
15 g MAC resin from a 30% dispersion
3 g 1,2-propylene glycol and
82 g water

EXAMPLE 8

The process according to Example 5 was carried out using
20 g MAC resin from a 30% dispersion
0.5 g ethoxylated partial glyceride of middle chain fatty acids
0.5 g glycerine and
79 g water

EXAMPLE 9

The process according to Example 5 was carried out using
25 g MAC resin from a 30% dispersion
6 g ethoxylated partial glyceride of middle chain fatty acids
0.25 g castor oil and
68.75 g water.

EXAMPLE 10

An air suspending equipment was charged with a quantity of ca. 16.8 kg 5 minim oval soft gelatin capsules. 500g of the intermediate layer solution according to Example 3 and thereafter 4 kg of the gastric juice resistant lacquer dispersion according to Example 9 were evaporated down on the capsules in the air suspension using a two component nozzle at a drying temperature of 40°C ± 2° C. After the lacquer had been applied, the capsules were left for a further 5 minutes in the vortex layer and the drying temperature simultaneously lowered. The capsules coated in this way were dried to hardness in a manner known per se.

EXAMPLE 11

An air suspending equipment was charged with a quantity of 2,500 hard gelatin capsules No. 1 with a filling weight of 250 mg. 250 g of the intermediate layer solution according to Example 1 and thereafter a quantity of 500 g of the gastric juice resistant lacquer dispersion according to Example 6 were evaporated down on the capsules in the air suspension using a two component nozzle at a drying temperature of 35°C ± 2°C. After application of the lacquer, the capsules were left for a further 5 minutes in the air suspension and subsequently dried to hardness in a manner known per se.

What is claimed is:

1. A gastric juice resistant gelatin capsule comprising a gelatin shell, a gastric juice resistant outer coating comprising an anionic polymerizate of methacrylic acid and acrylic acid esters, and an intermediate layer between said outer coating and the gelatin shell comprising a cationic polymerizate of di-lower alkylamino lower alkylmethacrylate with other neutral methacrylic esters, wherein lower alkyl is of 1 to 4 carbon atoms.

2. A gelatin capsule according to claim 1, wherein the intermediate layer comprises a copolymerizate of dimethylaminoethylmethacrylate, methacrylic acid butylester, and methacrylic acid methyl ester, said components being respectively present in a ratio of 50: 30: 20.

3. A gelatin capsule according to claim 1 wherein said intermediate layer is present in an amount of 0.25 mg – 2.5 mg resin/cm$^2$ of capsule surface area.

4. A gelatin capsule according to claim 1 wherein said gastric juice resistant outer coating is present in an amount of 2–20 mg resin/cm$^2$ of capsule surface area.

5. A process for producing a gastric juice resistant gelatin capsule comprising coating a gelatin capsule with a very thin, pore-free film comprising a cationic polymerizate of di-lower alkyl-amino lower alkyl methacrylate with other neutral methacrylic acid esters from an aqueous-alcoholic solution to form an intermediate layer, and thereafter coating said intermediate layer with a film of a gastric juice resistant coating comprising an anionic polymerizate of methacrylic acid and acrylic ester from an aqueous dispersion and wherein lower alkyl is 1 to 4 carbon atoms.

6. A process according to claim 5, characterized in that the intermediate layer is applied in a quantity of 0.25 mg - 2.5 mg resin/cm² capsule surface area.

7. A process according to claim 5 characterized in that the gastric juice resistant coating is applied to the intermediate layer in a quantity of 2 – 20 mg resin/cm² capsule surface area.

* * * * *